(12) United States Patent
Ambrus, Jr. et al.

(10) Patent No.: US 7,622,574 B2
(45) Date of Patent: Nov. 24, 2009

(54) IL-14α RNA INHIBITORS AND ANTIBODIES TO IL-14α FOR TREATMENT OF AUTOIMMUNE DISEASES AND LYMPHOMAS

(75) Inventors: Julian L. Ambrus, Jr., Buffalo, NY (US); Long Shen, Tonawanda, NY (US); Richard Ford, Houston, TX (US); Chongjie Zhang, Sichuan (CN)

(73) Assignee: The Research Foundation of State University of New York, Buffalo, NY (US)

( * ) Notice: Subject to any disclaimer, the term of this patent is extended or adjusted under 35 U.S.C. 154(b) by 125 days.

(21) Appl. No.: 11/977,778

(22) Filed: Oct. 26, 2007

(65) Prior Publication Data

US 2008/0146519 A1    Jun. 19, 2008

Related U.S. Application Data

(60) Provisional application No. 60/863,012, filed on Oct. 26, 2006.

(51) Int. Cl.
*C07H 21/04* (2006.01)
*A61K 31/70* (2006.01)
(52) U.S. Cl. .................. 536/24.5; 536/23.1; 514/44
(58) Field of Classification Search .................. None
See application file for complete search history.

(56) References Cited

FOREIGN PATENT DOCUMENTS

WO    WO 94/16074 A2    7/1994

OTHER PUBLICATIONS

Ambrus et al. PNAS 1993, vol. 90, pp. 6330-6334.*
Shen, et al.; Development of Autoimmunity in IL-14α-Transgenic Mice; The Journal of Immunology, 2006; pp. 5676-5686.

* cited by examiner

*Primary Examiner*—Tracy Vivlemore
(74) *Attorney, Agent, or Firm*—Hodgson Russ LLP

(57) ABSTRACT

Provided are antisense poly-2'-O-(2,4-dinitrophenyl)oligoribonucleotides which are complementary to the IL-14α gene and/or transcribed IL-14α mRNA. Also provided are monoclonal antibodies reactive with discreet IL-14α peptides. The oligoribonucleotides and monoclonal antibodies are useful in inhibiting the growth of lymphocytes.

7 Claims, 3 Drawing Sheets

```
                       SEQUENCE LISTING

<160> NUMBER OF SEQ ID NOS: 6

<210> SEQ ID NO 1
<211> LENGTH: 21
<212> TYPE: RNA
<213> ORGANISM: Homo sapiens

<400> SEQUENCE: 1
gcugcgggcc aggacggccu u                                              21

<210> SEQ ID NO 2
<211> LENGTH: 21
<212> TYPE: RNA
<213> ORGANISM: homo sapiens

<400> SEQUENCE: 2
gcaccagcug gcucugcuuu u                                              21

<210> SEQ ID NO 3
<211> LENGTH: 21
<212> TYPE: RNA
<213> ORGANISM: homo sapiens

<400> SEQUENCE: 3
gcgcaggugg uccuucucuu g                                              21

<210> SEQ ID NO 4
<211> LENGTH: 22
<212> TYPE: PRT
<213> ORGANISM: homo sapiens

<400> SEQUENCE: 4

Glu Arg Arg Pro Glu Gly Pro Gly Ala Gln Ala Pro Ser Ser Pro Arg
1               5                   10                  15

Val Thr Glu Ala Pro Cys
            20

<210> SEQ ID NO 5
<211> LENGTH: 21
<212> TYPE: PRT
<213> ORGANISM: homo sapiens

<400> SEQUENCE: 5

Cys Gln Gly Ser Leu Thr Asp Ser Gly Pro Glu Arg Arg Pro Glu Gly
1               5                   10                  15

Pro Gly Ala Gln Ala
            20
```

```
<210> SEQ ID NO 6
<211> LENGTH: 21
<212> TYPE: RNA
<213> ORGANISM: Artificial Sequence
<220> FEATURE:
<223> OTHER INFORMATION: Contains five mutations in IL-14alpha human
      sequence

<400> SEQUENCE: 6
gcggugagcc gguacggccu u                                              21
```

IL-14α RNA INHIBITORS AND ANTIBODIES TO IL-14α FOR TREATMENT OF AUTOIMMUNE DISEASES AND LYMPHOMAS

This application claims priority to U.S. Provisional Application No. 60/863,012 filed on Oct. 26, 2006, the disclosure of which is incorporated herein by reference.

FIELD OF THE INVENTION

This invention relates generally to antisense oligonucleotides and monoclonal antibodies directed to IL-14α.

BACKGROUND OF THE INVENTION

Interleukin 14α (IL-14α) is a cytokine that has been shown to participate in the formation and maintenance of normal B cell memory. Though the role of IL-14α in many immunological processes and diseases has remained poorly defined, there are some studies which suggest growth promoting activities of IL-14α for a limited number of B cell precursors, acute lymphocytic leukemia cells, most chronic lymphocytic leukemias (derived from B1 B cells), and all high-grade germinal center derived B cell malignancies, such as Burkitt lymphoma and Immunoblastic lymphoma. Thus, there is a need for compositions and methods that can alter the effects of IL-14α in autoimmune and cell proliferation disorders such as Systemic Lupus Erythromatoses (SLE), Sjogren's syndrome, and lymphomas of lymphoid origin.

SUMMARY OF THE INVENTION

The present invention provides antisense oligoribonucleotides which have complementary nucleic acid sequences that recognize and bind the human IL-14α gene and/or its mRNA, resulting in the down-regulation of transcription and/or translation of IL-14α, or function through an siRNA pathway. In one embodiment, the antisense oligoribonucleotides can be used to inhibit the proliferation of lymphocytes. Also provided are monoclonal antibodies (mAbs) reactive with particular IL-14α peptides. The mAbs are also useful for inhibiting the proliferation of lymphocytes.

DESCRIPTION OF THE INVENTION

Figure 1:
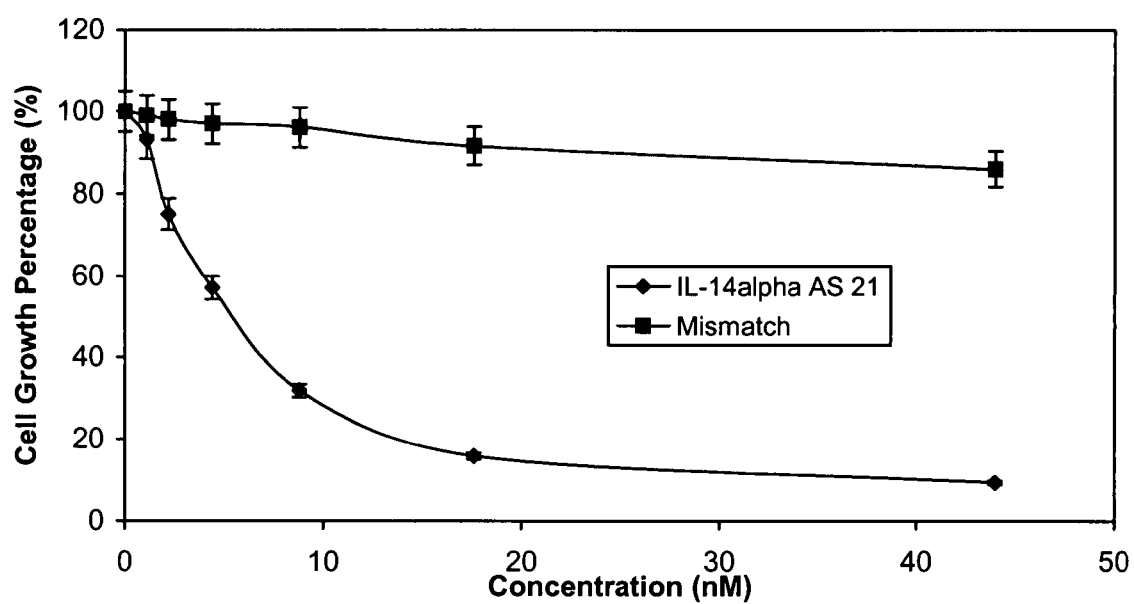
FIG. 1 provides a graphical representation of the inhibition of cell growth by poly-DNP-RNA data from inhibition of Namalva cell growth by poly-DNP-RNA targeted IL-14α at various poly-DNP-RNA concentrations.

The present invention provides antisense oligoribonucleotides which are complementary to target regions of the IL-14α gene or transcribed IL-14α mRNA. Without intending to be bound by any particular theory, it is considered that the antisense oligoribonucleotides act via down-regulation of DNA transcription or translation of IL-14α mRNA, or by functioning through an siRNA pathway. The antisense oligoribonucleotides are demonstrated to be capable of inhibiting the growth lymphoblastoid cells.

Three oligoribonucleotide sequences are provided herein. Accordingly, the oligoribonucleotides of the invention consist of the sequence GCUGCGGGCCAGGACGGCCUU (SEQ ID NO:1), also referred to as "IL-14alpha AS21"; GCACCAGCTGGCTCTGCUUUU (SEQ ID NO:2), also referred to as "IL-14alpha A1"; or GCGCAGGUGGUC-CUUCUCUUG (SEQ ID NO:3), also referred to as "IL-14alpha A2". Each of the ribose residues in these sequences are modified at the 2'-O-position with a 2'-O-(2,4-dinitrophenyl)-oligoribonucleotide (DNP) group as shown below to obtain poly-DNP-RNA.

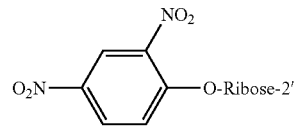

It will be recognized therefore that one or more ribose residues of the nucleotides of the present oligoribonucleotides can modified by the substitution of DNP at the 2'-O-position. In one embodiment, about 50-80% of the ribose residues are modified DNP. In another embodiment, about 65-75% of the ribose residues are modified by DNP. In yet another embodiment, 100% of the ribose residues are modified by DNP. Ribose residue groups that are not modified by DNP can be modified by other groups. Such modifying groups are known in the art and include but are not limited to 2'-O-methyl RNA(OME), 2'-O-methoxy-ethyl RNA (MOE) and 2'-fluoropyrimidine RNA.

The antisense oligonucleotides may be prepared by utilizing any known chemical oligonucleotide synthesis methods. Therefore, oligonucleotides can be made by using commercially available, automated nucleic acid synthesizers, such as the Applied Biosystems 380B DNA Synthesizer, which utilizes β-cyanoethyl phosphoramidite chemistry. Further, many antisense oligonucleotides are commercially available. For example, Oligo Therapeutics, Inc. has a broad line of commercially available oligonucleotides and, further, provides contract manufacturing services for the preparation of oligonucleotides. In addition, custom oligonucleotides can be made by IDT, Coralville, Iowa.

The synthesis and derivatization of single stranded RNA (ssRNA) can be carried out as follows. ssRNA is synthesized through in vitro transcription as described before (Milligan et al., 1987) with slight modification. A template containing T7 promoter can be synthesized (such as custom synthesis by commercial sources). After synthesis of the RNA, it can be derivatized by reaction with a suitable reagent such as 1-fluoro-2,4,-dinitrobenzene. The derivatized RNA is purified by the standard phenol/chloroform extraction and dialysis of the aqueous layer against water. The ratio of DNP to RNA and the actual concentration of poly DNP-RNA can be calculated from the observed absorbance at 260 and 330 nm since the oligonucleotide has absorbance only at 260 nm, whereas the DNP exhibits absorbance at both wavelengths. For larger scale synthesis, the product can be separated from the reaction mixture by column adsorption and gradient elution instead of dialysis.

The use of poly-DNP-RNA as a bioavailable platform for antisense RNAs has been demonstrated in the following publications: (1) Wang, A. and Wang, J. H. (1999) "Treatment of murine leukemia with poly-DNP-RNA", Antisense & Nucleic Acid Drug Development 9, 43-51; (2) Ru, K., Schmitt, S., James, W. I. and Wang, J. H. (1999) "Antitumor effect of antisense poly-DNP-RNA in vivo", Oncology Research 11, 505-572; (3) Ru, K., Taub, M. L. and Wang, J. H. (1998) "Antisense poly-DNP RNAs as specific breast cancer inhibitor", Oncology Research 10, 389-397; (4) Xin, W. and Wang, J. H. (1998), "Treatment of duck hepatitis B by poly-DNP-RNA", Antisense & Nucleic Drug Development 8, 459-468. Accordingly, it is expected that the oligoribonucloetides of the invention will be useful for administration to human individuals for prevention and/or therapy of conditions including but not limited to SLE, Sjogren's syndrome, and lymphomas of lymphoid origin. In this regard, efficacious non-toxic doses of the antisense oligoribonucleotides can be determined by clinicians having ordinary skill in the art. Typically, the dose may be selected such that it results in an extracellular concentration in the vicinity of the target cells that corresponds to what has been found to be effective as shown herein. For example, the dose may be selected from a range of 0.1 mg/kg to about 100 mg/kg, but is preferably less than 1 mg/kg. The dose can be administered to an individual orally, rectally, by injection, or continuously. It may also be delivered to the target site, such as a tumor, directly. When administered directly to the target site, a lower dose may be required. Even in the absence of transfection agents, poly-DNP-RNAs are slowly but spontaneously transported through mammalian cell membranes (Ashun et al., 1996; Ru et al., 1999). They are also not only resistant to hydrolysis by RNases, but may actually inhibit RNases including RNase H (Rahman et al., 1996).

For administration to individuals, the antisense oligoribonucleotides of the present invention can be incorporated into convenient pharmaceutical dosage forms such as capsules, tablets, injectable, topical or inhalable preparations. Solid or liquid pharmaceutical carriers can be employed. Solid carriers include, for example, starch, calcium, sulfate dehydrate, terra alba, sucrose, talc, gelatin, agar, pectin, acacia, magnesium stearate, and stearic acid. Liquid carriers include, for example, syrup, peanut oil, olive oil, saline and water. Liposomal, viral vector, and protein conjugate preparations can also be used as carriers. Similarly, the carrier or diluent may include any prolonged release material, such as glyceryl monostearate, or glyceryl disteararate, alone or with wax. The amount of solid carrier varies widely but preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension. When a liquid carrier is used, it will most often be a saline solution or phosphate buffered solution. For intranasal delivery, aerosolized preparations can be used.

Pharmaceutical preparations can be made following conventional techniques of a pharmaceutical chemist involving mixing, granulating and compressing, when necessary, for tablet forms, or mixing, filling, and dissolving the ingredients, as appropriate, to give the desired oral or parenteral products.

In another embodiment, the invention provides mAbs reactive with particular IL-14α peptides. In particular, two peptides were synthesized and used to raise mAbs, one peptide based on the N-terminus amino acid sequence of IL-14α (ERRPEGPGAQAPSSPRVTEAPC; SEQ ID NO:4, used to raise 1C6) and another peptide based on the C-terminus amino acid sequence of IL-14α (CQGSLTDSGPERRPEGP-GAQA; SEQ ID NO:5, used to raise 1F2). mAbs reactive against these peptides are expected to be useful for administration to human individuals for prevention and/or therapy of conditions including but not limited to SLE, Sjogren's syndrome, and lymphomas of lymphoid origin. In this regard, mAb 1C6 is demonstrated to be capable of inhibiting the proliferation of B lymphocytes, and proliferation of B lymphocytes is known to be associated with the aforementioned disorders. In this regard, for administration to humans the present invention contemplates making a "humanized" mAbs. "Humanized" forms of non-human (e.g., mice) antibodies are chimeric antibodies that contain minimal sequence derived from the non-human antibody. Humanized antibodies are essentially human immunoglobulins (also called the "recipient" antibody) in which residues from a hypervariable region of the recipient are replaced by residues from a hypervariable region of a non-human species (also called a "donor" antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also can comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Methods for humanizing non-human antibodies are well known in the art. For example, this can be essentially performed following the method of Winter and co-workers by substituting mouse CDR sequences for the corresponding sequences of a human antibody (Jones et al., Nature, 321:522-525 (1986); Riechmann et al., Nature, 332:323-327 (1988); Verhoeyen et al., Science, 239:1534-1536 (1988)).

In another embodiment, an antigen-binding or variable region fragment of mAbs may be used in the method of the invention. Suitable antibody fragments include Fab, Fab', F(ab')$_2$, Fv and scFv. Various techniques have been developed for the production of antibody fragments. Traditionally, these fragments were derived via proteolytic digestion of intact antibodies (see, e.g., Morimoto et al, Journal of Biochemical and Biophysical Methods 24:107-117 (1992) and Brennan et al., Science, 229:81 (1985)). However, these fragments can now be produced directly by recombinant host cells. For example, antibody fragments can be isolated from antibody phage libraries. Alternatively, Fab'-SH fragments can be directly recovered from *E. coli* and chemically coupled to form F(ab')2 fragments (Carter et al., Bio/Technology 10: 163-167 (1992)). According to another approach, F(ab')2 fragments can be isolated directly from recombinant host cell culture. Other techniques for the production of fragments of the mAbs of the present invention will be apparent to those skilled in the art.

In another embodiment, a mAb or antigen binding fragment thereof of the invention may be conjugated to a chemotherapeutic agent to enable localization of the chemotherapeutic agent to target cells. Chemotherapeutic agents useful in the generation of such antibody conjugates include enzymatically active toxins and fragments thereof. Suitable enzymatically active toxins include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

Conjugates of the mAbs and antigen binding fragments and chemotherapeutic agents may be made using a variety of bifunctional protein coupling agents such as N-succinimidyl-3-(2-pyriyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared essentially as described in Vitetta et al. Science 238: 1098 (1987

In another embodiment, the mAb may be conjugated to a radioactive agent. A variety of radioactive isotopes are available for conjugating to a mAb such that cells to which the mAb binds may be imaged or selectively destroyed. For selective destruction, the mAb may be conjugated to a highly radioactive atom, such as $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Therapeutic formulations comprising conjugated or unconjugated mAbs or antigen binding fragments thereof may be prepared by mixing with pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ PLURONICS™ or polyethylene glycol (PEG).

mAbs may be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the mAbs may suitably be administered by pulse infusion, e.g., with declining doses of the antibody.

One may also administer other compounds, such as chemotherapeutic agents, immunosuppressive agents and/or cytokines with the mAbs. The combined administration can include co-administration, using separate formulations or a single pharmaceutical formulation, and can also include consecutive administration in either order, wherein preferably there is a time period while both (or all) active agents simultaneously exert their biological activities.

The mAbs or antigen binding fragments thereof can be administered in a conventional dosage form prepared by combining with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables, such as the size of the individual and the stage of the disease.

This invention is further described in the examples provided below which are intended to be illustrative and are not intended to be restrictive in any way.

EXAMPLE 1

This example demonstrates inhibition of proliferation of human lymphoblastoid cells (Namalva cells) established from a Burkitt lymphoma using the oligoribonucleotides of the invention. In particular, FIG. 1 depicts sequence and concentration dependence of the inhibition of Namalva cell growth by poly-DNP-RNA targeted IL-14α. To obtain these data, the cells were plated at a concentration of $2 \times 10^5$ per well then treated with different concentrations of poly-DNP-RNA in the presence of oligofectamine. After incubation for 1 day the liquid was removed and replaced by fresh medium without poly-DNP-RNA and oligofectamine. After incubation of 7 more days, the cells were collected and counted with a Coulter counter. Data in FIG. 1 are expressed as the percentage of growth inhibition in reference to the growth of untreated control cells and are presented as means ±SD of four independent determinations.

As demonstrated in FIG. 1, IL-14alpha AS21 blocks IL-14α dependent proliferation of the lymphoma cells. The $IC_{50}$ value of IL-14alpha AS21 was determined to be approximately 5 nM. A control DNP-RNA consisting of the sequence GCGGUGAGCCGGUACGGCCUU (SEQ ID NO:6), which contains five mismatched nucleotides as compared to IL-14alpha AS21, had no effect on the growth of these cells. At the same time, alternative poly-DNP-RNA sequences were also demonstrated to have effect in blocking IL-14α activity. In particular, the $IC_{50}$ value of IL-14alpha A1 was determined to be approximately 25 nM, while the $IC_{50}$ value of IL-14 alpha A2 was determined to be approximately 15 nM.

EXAMPLE 2

Figure 2:
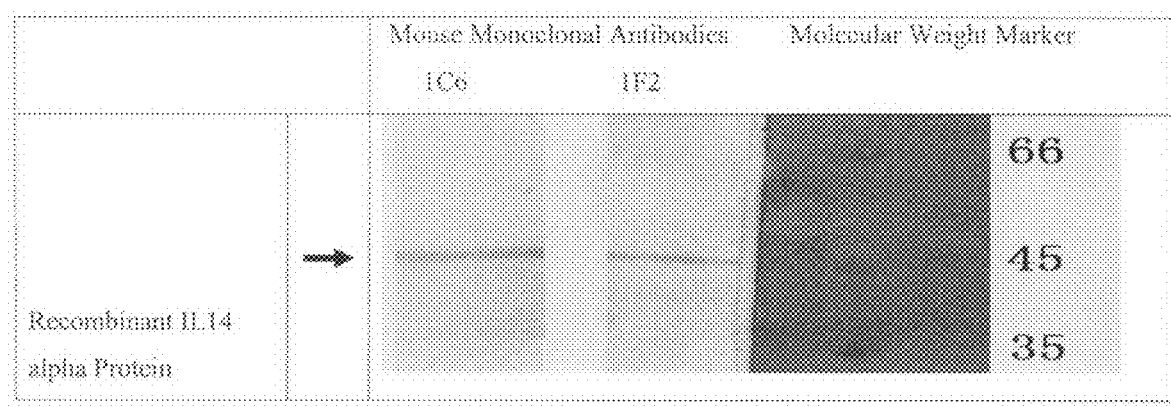
FIG. 2 is a photographic representation of a Western blot demonstrating binding of mAbs 1C6 and 1F2 to recognize recombinant IL-14α.

The example demonstrates the generation of mAbs of the invention. Peptide consisting of the sequence ERRPEGPGAQAPSSPRVTEAPC (SEQ ID NO:4) and CQGSLTDSGPERRPEGPGAQA (SEQ ID NO:5) were crosslinked with KLH by using a the commercially available DC crosslink kit from PIERCE® to generate antigen: IL-14alpha peptide conjugated with KLH. Balb/c female mice were immunized with IL—the peptide conjugated with KLH (200 µg per 500 µl) and incompleted Freud's adjuvant (500 µl) at day 0, 14 and 28. After immunization with antigen, spleen cells were collected from mice in day 31 and mixed with $SP_2/0$ cell at ratio of 10:1 and fused in 50% of PEG 4000. Cells were then cultured in the HAT selective medium for 7 days before changed to HT medium. After screening by ELISA assay, two hybridoma cell lines that can consistently secrete anti IL-14alpha antibody were established. The subclass of these antibodies is IgG2a κ. The affinity value of mAb 1 C6 was $6.16 \times E^{-09}$ mol/l and the affinity value of antibody of mAb 1F2 was $1.6 \times E^{-09}$ mol/l. FIG. 2 is a photographic representation of a Western blot demonstrating binding of mAbs 1C6 and 1F2 to recombinant IL-14α. Recombinant IL-14α was prepared using a conventional bacterial expression system.

EXAMPLE 3

Figure 3:
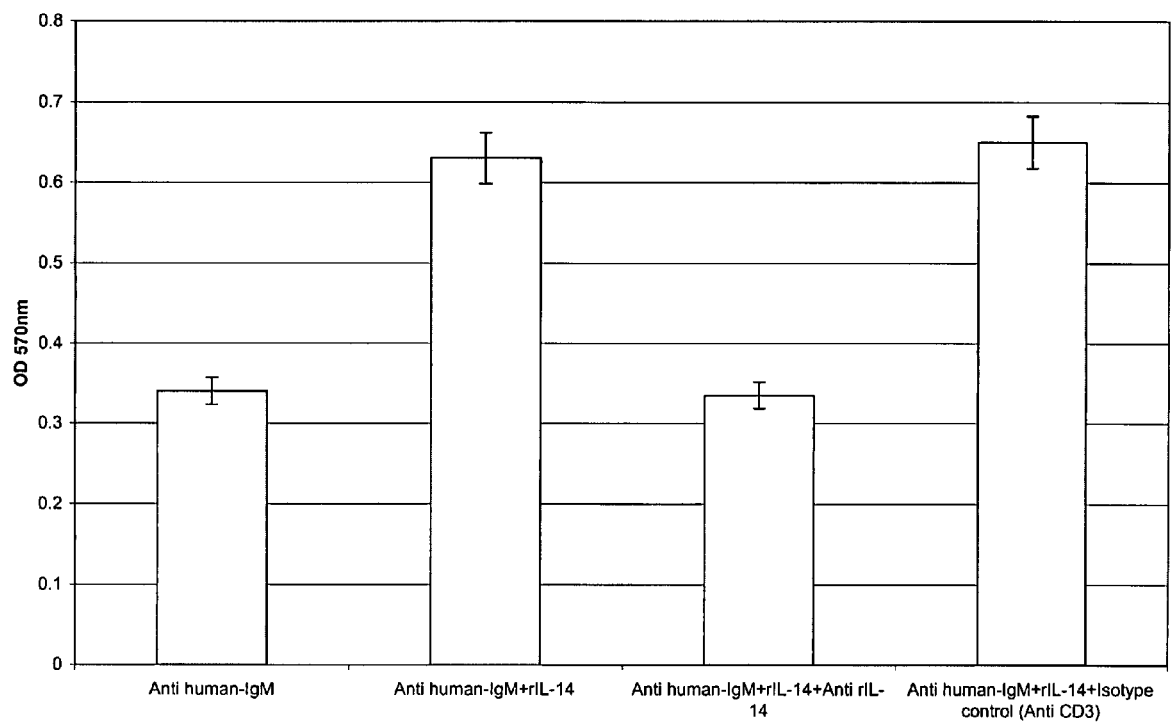
FIG. 3 provides a graphical representation of data from inhibition of B cell proliferation using mAb 1C6.

This example demonstrates that a mAb directed it IL-14α can be used to inhibit the growth of B cells. To obtain the data for this example, B cells (CD19+ cells) were purified with magnetic beads and plated at $10^5$ cells per well culture for 72 hour in the presence of anti-human IgM (1 μg/l), recombinant IL-14α (2.5 μg/ml), anti-IL-14α monoclonal antibody (2.5 mg/ml) and/or control antibody (anti-CD3, 2.5 μg/ml) as indicated. Proliferation was determined by conventional MTT assay at 72 hours. The data from this analysis are shown in FIG. 3. Shown are the mean and SEM for each condition run in quadruplicate wells. As can be seen from FIG. 3, administration of mAb 1C6 eliminated the proliferative effect of IL-14α on B cells.

While the present invention has been described using the above examples, routine modifications to this invention will be apparent to those skilled in the art and are intended to be within the scope of the invention.

We claim:

1. An isolated oligoribonucleotide consisting of SEQ ID NO:1, SEQ ID NO:2 or SEQ ID NO:3,
   wherein the ribose residue of at least one nucleotide in the oligoribonucleotide is protected at the 2'-O-position by 2,4-dinitrophenyl (DNP).

2. The oligoribonucleotide of claim 1, wherein the 50-80% of the ribose residues are protected by DNP.

3. The oligoribonucleotide of claim 2, wherein 65-75% of the ribose residues are modified by DNP.

4. The oligoribonucleotide of claim 1, wherein each nucleotide is protected at the 2'-O-position by DNP.

5. A composition comprising an oligoribonucleotide of claim 1.

6. The composition of claim 5, further comprising a pharmaceutically acceptable carrier.

7. The composition of claim 5, further comprising a chemotherapeutic agent.

* * * * *